(12) United States Patent
Kim et al.

(10) Patent No.: US 11,882,858 B2
(45) Date of Patent: Jan. 30, 2024

(54) COMPOSITION FOR SKIN WHITENING COMPRISING β-MANGOSTIN AS EFFECTIVE INGREDIENT

(71) Applicant: INDUSTRY-ACADEMIC COOPERATION FOUNDATION GYEONGSANG NATIONAL UNIVERSITY, Gyeongsangnam-do (KR)

(72) Inventors: Kwang Dong Kim, Gyeongsangnam-do (KR); Ji Yun Yoo, Gyeongsangnam-do (KR); Hyung Won Ryu, Daejeon (KR); Soojong Park, Chungcheongnam-do (KR); Kiwon Lee, Gyeongsangnam-do (KR); Ki Hun Park, Gyeongsangnam-do (KR); Sangseok Oh, Gyeongsangnam-do (KR)

(73) Assignee: INDUSTRY-ACADEMIC COOPERATION FOUNDATION GYEONGSANG NATIONAL UNIVERSITY, Gyeongsangnam-do (KR)

( * ) Notice: Subject to any disclaimer, the term of this patent is extended or adjusted under 35 U.S.C. 154(b) by 630 days.

(21) Appl. No.: 15/752,951

(22) PCT Filed: Sep. 20, 2016

(86) PCT No.: PCT/KR2016/010466
§ 371 (c)(1),
(2) Date: Feb. 15, 2018

(87) PCT Pub. No.: WO2017/052155
PCT Pub. Date: Mar. 30, 2017

(65) Prior Publication Data
US 2018/0256486 A1 Sep. 13, 2018

(30) Foreign Application Priority Data

Sep. 21, 2015 (KR) .................. 10-2015-0133301

(51) Int. Cl.
*A23L 33/105* (2016.01)
*A61Q 19/02* (2006.01)
*A61K 31/352* (2006.01)
*A61K 36/38* (2006.01)
*A61K 8/49* (2006.01)
*A61K 8/9789* (2017.01)
*A23L 29/206* (2016.01)
*A61K 8/9783* (2017.01)
*A61P 17/00* (2006.01)
*A61K 8/02* (2006.01)
*A61K 8/04* (2006.01)
*A61K 8/06* (2006.01)

(52) U.S. Cl.
CPC .......... *A23L 33/105* (2016.08); *A23L 29/206* (2016.08); *A61K 8/022* (2013.01); *A61K 8/042* (2013.01); *A61K 8/06* (2013.01); *A61K 8/498* (2013.01); *A61K 8/9783* (2017.08); *A61K 8/9789* (2017.08); *A61K 31/352* (2013.01); *A61K 36/38* (2013.01); *A61P 17/00* (2018.01); *A61Q 19/02* (2013.01); *A61K 2121/00* (2013.01); *A61K 2800/43* (2013.01); *A61K 2800/805* (2013.01)

(58) Field of Classification Search
CPC ... A23L 33/105; A23L 29/206; A61K 8/9783; A61K 8/9789; A61K 8/022; A61K 8/042; A61K 8/06; A61K 8/498; A61K 31/352; A61K 36/38; A61K 2121/00; A61K 2800/43; A61K 2800/805; A61P 17/00; A61Q 19/02
USPC ...................................................... 424/401
See application file for complete search history.

(56) References Cited

U.S. PATENT DOCUMENTS

2006/0292255 A1    12/2006   Moffett et al.
2007/0025951 A1*   2/2007    Foulger ............... A61K 8/92
                                                         424/74

FOREIGN PATENT DOCUMENTS

| CN | 103393576 A | 11/2013 |
|---|---|---|
| DE | 102008052341 A1 | 4/2010 |
| JP | H04244004 A | 9/1992 |
| JP | 2002-047180 A | 2/2002 |
| JP | 2007-106674 A | 4/2007 |
| JP | 2007-153773 A | 6/2007 |
| JP | 2012-131789 A | 7/2012 |
| KR | 10-1299013 B1 | 8/2013 |
| WO | WO 2005/048934 A2 | 6/2005 |

(Continued)

OTHER PUBLICATIONS

Lee et al. (Depigmentation of α-melanocyte-stimulating hormone-treated melanoma cells by β-mangostin is mediated by selective autophagy, Exp. Dermatol. 26(7):585-591 (abstract)). (Year: 2016).*

(Continued)

*Primary Examiner* — Adam C Milligan
(74) *Attorney, Agent, or Firm* — The PL Law Group, PLLC

(57) ABSTRACT

A skin whitening composition includes β-mangostin or a cosmetically acceptable salt thereof as an effective ingredient. β-Mangostin represented by Chemical Formula 1 suppresses the expression of tyrosinase and TRP-1 (tyrosinase-related protein-1) and induces autophagy of a melasosome. As such, it was confirmed that the β-mangostin not only suppresses melanin production but also exhibits the effect of removing previously formed melanin. Accordingly, the β-mangostin can be advantageously used as a functional material for skin whitening and skin lightening.

3 Claims, 9 Drawing Sheets
Specification includes a Sequence Listing.

(56) References Cited

FOREIGN PATENT DOCUMENTS

| WO | WO 2005/048940 A2 | 6/2005 |
|----|-------------------|--------|
| WO | WO 2006/137139 A1 | 12/2006 |
| WO | WO 2013/129334 A1 | 9/2013 |

OTHER PUBLICATIONS

Hyun-Ah Jung et al., "Antioxidant Xanthones from Pericarp of *Garcinia mangostana* (Mangosteen)", Journal of Agricultural and Food Chemistry, 2006, 54, p. 2077-2082.

International Search Report for PCT/KR2016/010466.

Arif, Nurul Jannah et al., "Development of Lightening Cream from Mangosteen Pericarp Extract with Olivoil Emulsifier", 2014 4th International Conference on Education, Research and Innovation, International Proceedings of Economics Development and Research, 2014, (81), p. 58-65.

Tadtong, Sarin et al., "Antityrosinase and Antibacterial Activities of Mangosteen Pericarp Extract", Journal of Health Research, 2009, 23(2), p. 99-102.

Jennifer, C. et al., "A Review on Skin Whitening Property of Plant Extracts", International Journal of Pharma and Bio Sciences, 2012, 3(4), B332-B347.

Hyung Won Ryu et al. "a-Glucosidase inhibition and antihyperglycemic activity of prenylated xanthones from Garcinia mangostana", 2011, Phytochemistry 72, 2148-54.

Jeong-yeh Yang et al., "Stimulation of melanogenesis by scoparone in B16 melanoma cells", 2006, Acta pharmacologica Sinica 27, 1467-73.

Ohgushi et al., "Effects of Sesquiterpene Lactones on Melanogenesis in Mouse B16 Melanoma Cells", 2009, Biological & pharmaceutical bulletin 32, 308-10.

Shunsuke Kimura et al., "Dissection of the Autophagosome Maturation Process by a Novel Reporter Protein, Tandem Fluorescent-Tagged LC3", 2007, Autophagy 3, 452-60.

\* cited by examiner (A)

(B)

ID

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
ggccagcttt caggcagagg t                                           21

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
tggtgcttca tgggcaaaat c                                           21

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
gctgcaggag ccttctttct c                                           21

<210> SEQ ID NO 4
<211> LENGTH: 21
<212> TYPE: DNA
<213> ORGANISM: Artificial Sequence
```

```
<220> FEATURE:
<223> OTHER INFORMATION: primer

<400> SEQUENCE: 4
aagacgctgc actgctggtc t                                           21
```

COMPOSITION FOR SKIN WHITENING COMPRISING β-MANGOSTIN AS EFFECTIVE INGREDIENT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2016/010466, filed Sep. 20, 2016, which claims priority to the benefit of Korean Patent Application No. 10-2015-0133301 filed in the Korean Intellectual Property Office on Sep. 21, 2015, the entire contents of which are incorporated herein by reference.

TECHNICAL FIELD

The present invention relates to a composition for skin whitening comprising β-mangostin as an effective ingredient. More specifically, the present invention relates to a composition having a skin whitening function containing beta-mangostin, which is derived from mangosteen (*Garcinia mangostana*), characterized by inhibition of melanin production and reduction of previously formed melanin through suppressing the activities of tyrosinase and TRP-1 (tyrosinase-related protein-1).

BACKGROUND ART

Among the tissues of a human body, skin is directly exposed to an external environment and plays a role of a protective wall between the inside of a human body and an external environment. It provides a protection against external environment-contaminating substances including chemical substances, ultraviolet rays and invasion by microorganisms, and thus protects a living body from a surrounding environment. Skin color is determined by melanin, hemoglobin, carotene, or the like, and melanin plays the most important role among them. In addition to the determination of human skin color, melanin performs a skin protection function like ultraviolet absorption activity, activity of a free radical scavenger, or the like. However, when excessive production of melanin is caused by a change in external environment like excessive exposure to ultraviolet rays, air pollution, stress, or the like, the pigmentation phenomenon occurs in skin to yield skin melanism, small brown spots, freckles, or the like. Skin melanism is caused by the reaction of skin cells against internal and external factors, and the most representative cause is exposure to ultraviolet rays. Namely, once a skin is exposed to ultraviolet rays, tyrosinase is activated. As the tyrosinase activates tyrosine present in skin tissue to oxidize DOPA (dihydroxyphenylalanine) and dopaquinone to produce melanin in the melanocyte of skin pigment cell, melanocyte. This melanin is transferred to keratinocyte of skin and protects skin from ultraviolet rays by keratinization process. As such, melanin is an ultraviolet protecting agent that is essentially required in human body, and it also plays a role of an effective free radical scavenger for removing various radicals that can cause deformation of biological components like protein, lipid, and nucleic acid. However, if there is locally excessive production of melanin or deterioration of a physiological function of skin which is diminished by aging or skin lesion, melanin is precipitated on a skin surface to yield small brown spots, freckles, and various pigmentations. Since the cause and mechanism of skin melanism are known as described in the above, for producing skin whitening cosmetics, a method of blending materials having an inhibitory effect on the activity of tyrosinase, which is an enzyme involved with a skin melanism process, or a method of reducing melanin production by inhibiting part of the reactions during melanin production process is generally used. Representative materials used for such purpose include chemical materials such as ascorbic acid, kojic acid, or hydroquinone, and plant extracts such as mulberry root skin extract or liquorice extract. However, ascorbic acid is not suitable as a melanin production inhibitor because it has not only an insufficient inhibitory effect on tyrosinase activity but also poor stability of the molecule itself. Although kojic acid is excellent in inhibitory activity on tyrosinase, there is a problem in terms of the stability like discoloration after blending in cosmetic materials and lower potency according to a change over time, and, due to significant skin irritation, it has a limitation in terms of actual use. Use of hydroquinone as a cosmetic material is also limited due to a problem related to skin irritation and safety. Therefore, there is growing interest in development of a novel and effective skin whitening component.

Mangosteen (*Garcinia mangostana*) is an evergreen tree belonging to Staphyleaceae of Sapindales as a dicot plant originated in Malaysia. It has a sweet and sour flavor, and tastes very good so that it is referred to as the queen of all tree fruits. The pigment present in fruit flesh of mangosteen includes tannin, and thus discoloration does not easily occur. Thus, the pigment can be used as a dye. Instead of having fertilization, mangosteen is cultivated by growing seeds. As such, the same variety has been cultivated for a long time, and it is known to grow only in a limited area due to a difficulty in cultivation. Mangosteen grows mainly in Indonesia, Malaysia, Taiwan, Philippine., India, Sri Lanka, or the like. Mangosteen has a bactericidal activity, an anti-bacterial activity, and an anti-allergic activity, and by containing a large amount of beta carotene, it is known to inhibit the production of nitrosoamine as a carcinogen. Mangosteen is also known to be effective for osteoporosis prevention, eyesight improvement, appetite enhancement, digestion promotion, constipation prevention, activation of liver activity, tuberculosis prevention, heart protection, or the like. It is reported that the shell of mangosteen contains a large of amount of xanthone, which is reported to exhibit such favorable pharmaceutical effects.

Meanwhile, in Japanese Patent Application Laid-Open No. 2007-153773, xanthone derivatives, and a preparation for external skin application and a pharmaceutical composition containing the derivatives are disclosed, and in Korean Patent Registration No. 1299013, a composition comprising mangosteen extract for treating a pigmentation disorder is disclosed. However, there is no disclosure relating to a composition for skin whitening comprising, as an effective ingredient, β-mangostin derived from mangosteen of the present invention.

SUMMARY

The present invention is devised in view of the demand described above. The inventors of the present invention isolated β-mangostin from mangosteen seedcases, and confirmed that β-mangostin of the present invention not only suppresses melanin production but also exhibits the effect of removing previously formed melanin through the suppression of tyrosinase and TRP-1 (tyrosinase-related protein-1) and the induction of autophagy on melasosomes. The present invention is completed accordingly.

In order to achieve the object described above, the present invention provides a cosmetic composition for skin whitening comprising β-mangostin or a cosmetically acceptable salt thereof as an effective ingredient.

The present invention further provides a pharmaceutical composition for preventing or treating a melanin hyperpigmentation disorder comprising β-mangostin or a pharmaceutically acceptable salt thereof as an effective ingredient.

The present invention still further provides a functional health food composition for preventing or improving a melanin hyperpigmentation disorder comprising β-mangostin or a pharmaceutically acceptable salt thereof as an effective ingredient.

The present invention relates to a composition for skin whitening comprising β-mangostin as an effective ingredient. β-Mangostin of the present invention suppresses the expression of tyrosinase and TRP-1 (tyrosinase-related protein-1) and induces autophagy on melasosomes. Thus, it was confirmed that β-mangostin of the present invention not only suppresses melanin production but also exhibits the effect of removing melanin previously produced by α-MSH (melanocyte-stimulating hormone). As such, β-mangostin of the present invention can be advantageously used as a functional material for skin whitening and skin lightening.

DETAILED DESCRIPTION

Figure 1:
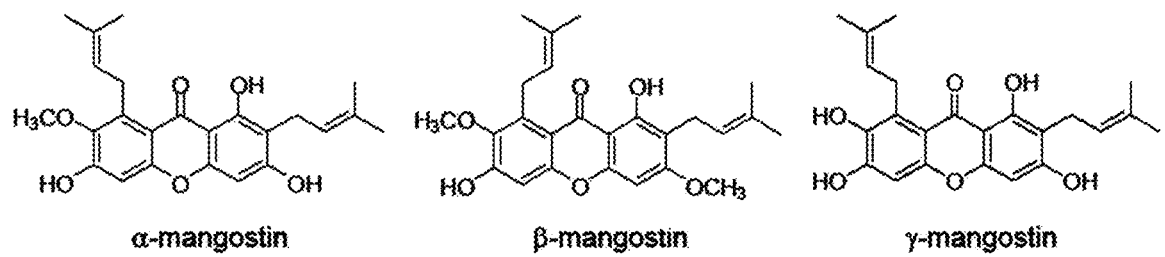
FIG. 1 shows the chemical structure of α-, β-, and γ-mangostin according to one embodiment of the present invention, which are xanthone series isolated and purified from seedcases of mangosteen (*Garcinia mangostana*).

To achieve the object of the present invention, the present invention provides a cosmetic composition for skin whitening comprising β-mangostin represented by the following chemical formula 1 or a cosmetically acceptable salt thereof as an effective ingredient.

[Chemical formula 1]

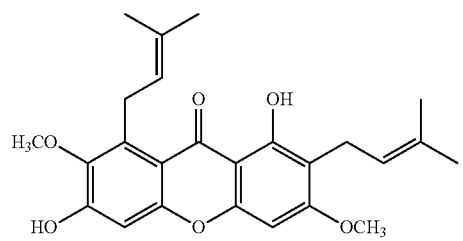

The effective ingredient of the cosmetic composition for skin whitening according to the present invention is β-mangostin which has a structure represented by the above chemical formula 1. β-Mangostin of the present invention reduces melanin production and previously formed melanin in melanin cells in significant sense, and thus has an activity of skin whitening.

As for the cosmetically acceptable salt which can be used as an effective ingredient of the composition of the present invention, an acid addition salt formed with a cosmetically acceptable free acid is useful. The acid addition salt can be produced by a common method, e.g., a compound is dissolved in an excessive amount of an aqueous acid solution and the resulting salt is precipitated by using a water-miscible organic solvent such as methanol, ethanol, acetone, or acetonitrile. It is also possible that the compound and acid or alcohol (e.g., glycol monomethyl ether) in water, both in an equimolar amount, are heated and subsequently the mixture is dried by evaporation, or precipitated salts are filtered by suction. In that case, an organic acid or an inorganic acid can be used as a free acid. As for the inorganic acid, hydrochloric acid, phosphoric acid, sulfuric acid, nitric acid, stannic acid, or the like can be used, and as for the organic acid, methane sulfonic acid, p-toluene sulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, or the like can be used, but the inorganic acid and organic acid are not limited to them.

Meanwhile, the skin whitening effect intends to mean an effect of improving or preventing darkish skin, small brown spots, freckles, or dark circles which occur due to various causes including exposure to ultraviolet rays, a change in hormone balance, or a genetic program, an effect of obtaining a beautiful skin with translucent feel or maintaining a beautiful skin with translucent feel, or an effect of enhancing shine and tight feeling by reducing the darkish feeling of a skin. In general, a darkish skin, small brown spots, freckles, or dark circles are known to occur due to the precipitation of biosynthesized melanin pigment on skin as melanocytes are stimulated by ultraviolet rays or a change in hormone balance. Accordingly, if melanin production is suppressed, it becomes possible to prevent or improve a darkish skin, small brown spots, freckles, or dark circles.

The function of β-mangostin to suppress melanin production was determined by a test method in which cultured pigment cells are used. The pigment cells indicate cells which have a function of producing melanin, and when they are cultured in general, melanin pigment is precipitated to yield dark pigmentation. On the other hand, if a material having a function of suppressing melanin production is present in the culture system, the melanin production is suppressed to yield relative whitening. Based on the degree of this relative whitening, the function of suppressing melanin production can be predicted.

According to the cosmetic composition for skin whitening of the present invention, β-mangostin may be β-mangostin which has been isolated from seedcases of a mangosteen, but it is not limited thereto.

According to the cosmetic composition for skin whitening of the present invention, β-mangostin may be β-mangostin which has been isolated by extraction of seedcases of a mangosteen with chloroform, but it is not limited thereto.

According to the cosmetic composition for skin whitening of the present invention, the β-mangostin may inhibit the activities of tyrosinase or TRP-1 (tyrosinase-related protein-1), but it is not limited thereto.

According to the cosmetic composition for skin whitening of the present invention, the β-mangostin may suppress production of melanin or remove previously-produced melanin, but it is not limited thereto.

According to the cosmetic composition for skin whitening of the present invention, the cosmetic composition for skin whitening can have any one formulation selected from a group consisting of an ointment for external skin application, a crème, a softening cosmetic water, a nutritional cosmetic water, a pack, an essence, a hair toner, a shampoo, a rinse, a hair conditioner, a hair treatment, a gel, a skin lotion, a skin softener, a skin toner, an astringent, a lotion, a milk lotion, a moisture lotion, a nutritional lotion, a massage crème, a nutritional crème, a moisture crème, a hand crème, a foundation, a nutritional essence, a sunscreen, a soap, a cleansing foam, a cleansing lotion, a cleansing crème, a body lotion, and a body cleanser, but it is not limited thereto. The cosmetic composition constituting each of those formulations may contain various bases and additives that are necessary and suitable for preparing those formulations, and the type and amount of the components can be easily selected by a person skilled in the pertinent art.

The cosmetic composition of the present invention may further contain, other than the effective ingredient, one or more kinds of a skin whitening active component which exhibits the same or similar activity. Examples of the skin whitening active component include kojic acid and derivatives thereof, albutin, ascorbic acid and derivatives thereof, hydroquinone and derivatives thereof, resorcinol, cycloalkanone, methylene dioxyphenylalkanol, 2,7-dinitroindazole, and plant extracts such as bearberry extract, rice extract, or liquorice extract, but it is not limited thereto.

In a case in which the cosmetic composition of the present invention has a formulation of paste, crème, or gel, animal fibers, plant fibers, wax, paraffin, starch, tragacanth, cellulose derivatives, polyethylene glycol, silicone, bentonite, silica, talc, or zinc oxide can be used as a carrier component.

In a case in which the cosmetic composition of the present invention has a formulation of powder or spray, lactose, talc, silica, aluminum hydroxide, calcium silicate, or polyamide powder can be used as a carrier component. In a case in which the cosmetic composition is a spray, in particular, a propellant such as chlorofluorohydrocarbon, propane-butane, or dimethyl ether can be additionally included.

In a case in which the cosmetic composition of the present invention has a formulation of solution or emulsion, a solvent, a solubilizing agent, or an emulsifying agent is used as a carrier component, and examples thereof include water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, and fatty acid ester of sorbitan.

In a case in which the cosmetic composition of the present invention has a formulation of suspension, a liquid phase diluent such as water, ethanol or propylene glycol, a suspending agent such as ethoxylated isostearyl alcohol, polyoxyethylene sorbitol ester, or polyoxyethylene sorbitan ester, microcrystalline cellulose, aluminum metahydroxide, bentonite, agar, or tragacanth can be used as a carrier component.

In a case in which the cosmetic composition of the present invention has a formulation of surfactant-containing cleanser, aliphatic alcohol sulfate, aliphatic alcohol ether sulfate, sulfonsuccinic acid monoester, acethionate, imidazolium derivatives, methyl taurate, sarcosinate, fatty acid amide ether sulfate, alkylamidobetain, aliphatic alcohol, fatty acid glyceride, fatty acid diethanolamide, plant oil, linolin derivatives, or ethoxylated glycerol fatty acid ester can be used.

The cosmetic composition of the present invention may additionally contain a vehicle including a fluorescent material, a bactericidal agent, a hydrotrope, a moisturizing agent, an aroma, an aromatic carrier, a protein, a solubilizing agent, sugar derivatives, a sunshine blocking agent, a vitamin, a plant extract, or the like.

The present invention further provides a pharmaceutical composition for preventing or treating a melanin hyperpigmentation disorder comprising β-mangostin or a pharmaceutically acceptable salt thereof as an effective ingredient.

The salt is not particularly limited as long as it is pharmaceutically acceptable, and hydrochloric acid, sulfuric acid, nitric acid, phosphoric acid, hydrogen fluoride acid, hydrogen bromide acid, formic acid, acetic acid, tartaric acid, lactic acid, citric acid, fumaric acid, maleic acid, succinic acid, methane sulfonic acid, benzene sulfonic acid, toluene sulfonic acid, naphthalene sulfonic acid, or the like can be used, for example. Other than the acid addition salt, a base addition salt such as sodium hydroxide, potassium hydroxide, triethylamine, or tertiary butylamine can be also used.

The term "melanin hyperpigmentation" used in this specification means blackening or darkening of a certain area of a skin, a finger nail, or a toe nail as caused by excessively increased melanin when compared to other area. Examples of the melanin hyperpigmentation include freckles, senile spots, chloasma, small brown spots, brown or black moles, sunshine pigment spots, cyanic melisma, hyperpigmentation after drug use, gravidic chloasma, hyperpigmentation after inflammation caused by lesions or skin inflammation like excoriation and burn, but it is not limited thereto.

The pharmaceutical composition of the present invention may contain a pharmaceutically acceptable carrier in addition to the effective ingredient. The carrier is a material which is commonly used for producing a preparation, and examples thereof include lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methylhydroxybenzoate, propylhydroxybenzoate, talc, magnesium stearate, and mineral oil, but it is not limited thereto. The pharmaceutical composition of the present invention may additionally contain, other than those components, a lubricating agent, a humidifying agent, a sweetening agent, a flavoring agent, an emulsifying agent, a suspending agent, a preservative, or the like. Suitable pharmaceutically acceptable carriers and preparations are described in detail in Remington's Pharmaceutical Sciences, 19th ed., 1995.

Preferable dosage of the pharmaceutical composition of the present invention may vary depending on various factors like a method for preparation, administration mode, age, weight, and state of a patient, food, administration period, administration route, excretion rate, and response sensitivity. Meanwhile, the dosage of the pharmaceutical composition of the present invention is preferably 0.0001 to 100 mg/kg of bodyweight per day.

The pharmaceutical composition of the present invention can be administered either orally or parenterally, and in case of parenteral administration, the administration can be made by topical application on skin, intravenous injection, subcutaneous injection, intramuscular injection, peritoneal injection, or transdermal administration. Considering that the pharmaceutical composition of the present invention is used for a treatment or a prophylaxis of a melanin hyperpigmentation disorder, the administration is preferably achieved by topical application of the composition on skin.

Concentration of the effective ingredient which is included in the composition of the present invention can be determined in consideration of treatment purpose, state of a patient, required period, or the like, and it is not limited to the concentration of a specific range.

The pharmaceutical composition of the present invention can be produced in unit dose form or by adding it to a multi-dose container according to formulation using a pharmaceutically acceptable carrier or vehicle by following a method that can be easily carried out by a person who has common knowledge in the field to which the present invention pertains. In that case, the formulation can be any one formulation selected from an injection solution, a crème, a patch, a spray, an ointment, a hard solid, a lotion, a liniment, a pasta, and a cataplasma, and a dispersing agent or a stabilizing agent may be additionally contained therein.

The present invention still further provides a functional health food composition for preventing or improving a melanin hyperpigmentation disorder comprising β-mangostin or a pharmaceutically acceptable salt thereof as an effective ingredient.

In a case in which the functional health food composition of the present invention is used as a food additive, the functional health food composition can be added directly or used with other food or other components, and it can be suitably used according to a common method. The mixing amount of the effective ingredient can be suitably used according to the purpose of use (i.e., prophylaxis or amelioration). In general, for producing a food product or a drink, the functional health food composition of the present invention is added in an amount of 15 part by weight or less, and preferably 10 parts by weight or less relative to the raw materials. However, in case of application for a long period of time like achieving health and hygiene, or having health management, the amount may be lower than the aforementioned range as there is no problem in terms of the safety, and thus the effective ingredient may be also used in an amount that is higher than the aforementioned range.

Type of the functional health food is not particularly limited. Examples of the food to which the functional health food composition can be added include meat, sausage, bread, chocolate, candies, snacks, biscuits, pizza, ramen, other noodles, gums, dairy products including ice cream, various kinds of soup, beverage, tea, drink, alcohol beverage, and vitamin complex, and all health foods in general sense are included therein.

The functional health food composition of the present invention can be also prepared as a food, in particular, a functional food. The functional food according to the present invention contains the components that are generally added for preparing a food, and examples thereof include proteins, carbohydrate, fats, nutrients, and flavoring agents. When it is prepared as a drink, for example, natural carbohydrates or a flavoring agent may be included as an additional component other than the effective ingredient. The natural carbohydrates are preferably monosaccharides (for example, glucose, fructose, and the like), disaccharides (for example, maltose, sucrose, and the like), oligosaccharides, polysaccharides (for example, dextrin, cyclodextrin, and the like), or sugar alcohols (for example, xylitol, sorbitol, erythritol, and the like). As for the flavoring agent, a natural flavoring agent (for example, thaumatin, stevia extract, and the like) and a synthetic flavoring agent (for example, saccharine, aspartame, and the like) can be used.

Other than those described above, the functional health food composition may further contain various kinds of a nutritional agent, vitamins, an electrolyte, flavors, a coloring agent, pectinic acid and salts thereof, alginic acid and salts thereof, organic acids, a protective colloid thickening agent, a pH adjusting agent, a stabilizing agent, a preservative, glycerin, alcohol, and a carbonating agent used for carbonate drink. Although the ratio of those components to be added is not critically important, it is generally selected from a range of from 0.01 to 0.1 part by weight relative to 100 parts by weight of the functional health food composition of the present invention.

Hereinbelow, the present invention is explained in greater detail in view of the Examples. However, it is evident that the following Examples are given only for specific explanation of the present invention and it would be obvious to a person who has common knowledge in the pertinent art that by no means the present invention is limited to the following Examples.

Materials and Methods

1. Sample Preparation

Mangosteen (*Garcinia mangostana*) seedcases were collected from Vietnam, and provided from LanSea Food on August, 2009. The voucher specimen was kept in a plant sample room of Kyungbuk National University, South Korea.

2. Isolation and Extraction of β-Mangostin

In order to isolate and extract β-mangostin, 0.5 kg of dried mangosteen seedcases was prepared as powder, and subjected to extraction with chloroform at room temperature. The extract was concentrated by using a device for concentration under reduced pressure. To remove completely the solvent which has been used for obtaining darkish red residues (65.6 g), it was kept in a dryer. Part of the residuals (5 g) was subjected to silica gel column (5×50 cm, 230 to 400 mesh, 500 g) chromatography [30:1 (1.5 L), 15:1 (1.5 L), 10:1 (1.5 L), 8:1 (1.5 L), 6:1 (1.5 L), 4:1 (1.5 L), 1:1 (1.5 L) and acetone (2 L)] with stepwise gradient of n-hexane and acetone. Based on comparison using thin layer chromatography profile, division into five small fractions was made (i.e., CC1 to CC5). The small fraction CC2 from which β-mangostin (252 mg) is obtained was subjected to flash column chromatography in which hexane/ethyl acetate gradient (30:1→1:1) is used. The small fraction CC3 having rich α-mangostin from which α-mangostin (2453 mg) is obtained was subjected to flash column chromatography in which hexane/ethyl acetate gradient (20:1→1:1) is used. The small fraction CC4 having rich γ-mangostin from which γ-mangostin (415 mg) is obtained was subjected to flash column chromatography in which hexane/ethyl acetate gradient (15:1→1:1) is used. The purified compounds were identified by comparing the $^1$H and $^{13}$C NMR data of the present invention with the data of the literature which has been published before (Ryu et al., 2011, Phytochemistry 72, 2148-54).

3. Cell Culture and Compounds

B16F10 mouse melanoma cell line was provided by ATCC (American Type of Culture Collection, USA). The cells were cultured in DME (Dulbecco's Modified Eagle's), which has been added with 10% FBS (fetal bovine serum) and 1% penicillin/streptomycin (Sigma-Aldrich, USA), in a 5% $CO_2$ humidifying incubator at 37° C. condition. α-MSH (melanocyte-stimulating hormone), bafilomycin A1, 3-MA (3-methyladenine), and chloroquine were purchased from Sigma-Aldrich, USA, tyrosine-EDTA was purchased from Lonza, USA, and MTT ([3-(4,5-dimethylthiazol-2-yl)-2,5-diphenyl tetrazolium bromide) was purchased from Amresco, USA, and they were used for the following Examples.

4. Measurement of Cell Viability

B16F10 cells were cultured for 24 hours in a 96-well plate. Thereafter, they were treated with α-, β- and γ-mangostin at various concentrations, and cultured for 24 hours. Subsequently, a MTT solution (5 μg/mL) was added to the cells, which were then cultured for 3 hours. After removing the medium and treating the cells with DMSO, the cells were cultured for 20 minutes. By using a microplate reader (Bio-Rad), absorbance at 595 nm was measured.

5. Measurement of Melanin Content

Measurement of melanin content was carried out by slightly modifying the method by Yang et al. (Yang et al., 2006, Acta pharmacologica Sinica 27, 1467-73). Specifically, B16F10 cells were inoculated into a 6-well plate and cultured for 24 hours. Thereafter, the cells were treated with β-mangostin and α-MSH, each at 1 μM, followed by culture for 48 hours. The cultured cells were collected after being subjected to trypsinization and dissolution in 1 N NaOH containing DMSO for 24 hours at 65° C. By using a microplate reader (Bio-Rad), melanin content was measured at 415 nm.

6. Measurement of Tyrosinase Activity

Tyrosinase activity was measured by slightly modifying the method by Ohgushi et al. (Ohgushi et al., 2009, Biological & Pharmaceutical Bulletin 32, 308-10). Specifically, B16F10 cells were inoculated into a 6-well plate and cultured for 24 hours. Thereafter, the cells were treated with β-mangostin and α-MSH, each at 1 μM, followed by culture for 48 hours. The cultured cells were collected and dissolved with 1% Triton X-100 solution for 1 hour on ice. The proteins were cultured with 100 μl (2 mg/ml) L-DOPA in a 5% $CO_2$ humidifying incubator at 37° C. condition. By using a microplate reader (Bio-Rad), absorbance at 490 nm was measured.

7. RNA Extraction and RT-PCR

Total RNA was extracted from the cells by using RiboEX reagent (GeneAll Biotechnology Co. Ltd, Seoul, South Korea). cDNA was synthesized by using 2 μg of RNA based on reverse transcription (Thermo Scientific, Waltham, MA, USA). PCR was carried out by using Solg™ e-Taq DNA polymerase kit (SolGent Co. Ltd, Daejeon, South Korea), and each primer described in the following Table 1 was used for PCR.

TABLE 1

Primers used in the present invention

| Target gene | SEQ ID No. | Forward direction/ Reverse direction | Nucleotide sequence |
|---|---|---|---|
| Tyrosinase | 1 | Forward direction | GGCCAGCTTTCAGGCAGAGGT (SEQ ID NO: 1) |
| | 2 | Reverse direction | TGGTGCTTCATGGGCAAAATC (SEQ ID NO: 2) |
| TRP-1 | 3 | Forward direction | GCTGCAGGAGCCTTCTTTCTC (SEQ ID NO: 3) |
| | 4 | Reverse direction | AAGACGCTGCACTGCTGGTCT (SEQ ID NO: 4) |

8. Western Blot Analysis

Total proteins were extracted by using RIPA dissolving buffer (50 mM Tris-HCl (pH 8.0), 150 mM NaCl, 1% NP-40, 0.5% sodium dioxycholate and 0.1% SDS). The proteins were separated on a 10 to 15% SDS-PAGE, and transferred to a PVDF membrane (Millipore, Billerica, MA, USA). The membrane was then incubated with 5% skim milk and primary antibody for 1 hour in TBS (tris-buffer saline) containing 0.1% Tween 20. The antibodies against tyrosinase and TRP-1 were purchased from Santa Cruz Biotechnology, USA. LC3B, p62 and ATG5 were purchased from CST (Cell Signaling Technology, USA). The antibody against PMEL was purchased from Abcam (UK). Signal detection was made based on enhanced chemiluminescence (Bio-Rad).

9. Gene Transfer and Gene Silencing

B16F10 cells were infected with mRFP-EGFP-LC3B (Kimura et al., 2007, Autophagy 3, 452-60) by using Lipofectamine 3000 (Invitrogen, Carlsbad, CA, USA). The cells were treated with β-mangostin (10 μM) and α-MSH (1 μM), and analysis was made by using confocal microscopy (FV1000, Olympus, Tokyo, Japan).

siRNA made suitable to mouse ATG5 siRNA was synthesized from Genolution (Seoul, South Korea). B16F10 cells were infected with siATG5 by using Lipofectamine 3000 (Invitrogen, Carlsbad, CA, USA) according to the manufacturer's instructions. After treating the cells with β-mangostin (10 μM) and α-MSH (1 μM) for 48 hours, the results were determined.

10. Statistical Analysis

All data were analyzed by using unpaired Student's t-test, and the results were considered to be statistically significant in case of having P<0.05.

Figure 2:
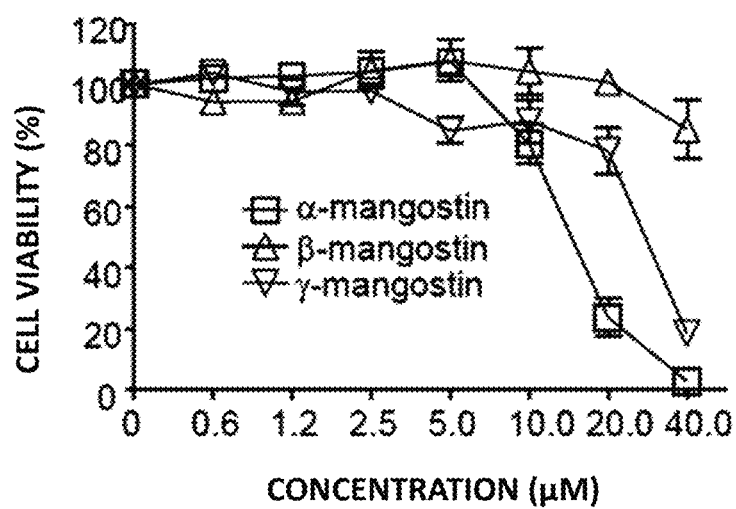
FIG. 2 shows cell viability when B16F10 mouse melanoma cells are treated with the indicated concentrations of α-, β-, and γ-mangostin according to one embodiment of the present invention.

Example 1. Analysis of Cell Viability According to Treatment with β-Mangostin of the Present Invention In Example 1, to find out functional plant metabolites which induce depigmentation in melanin cells, α-, β- and γ-mangostin, which are 3 kinds of edible xanthones, were isolated and purified from mangosteen (*Garcinia mangostana*) seedcases (FIG. 1). To determine the cytotoxicity of those 3 kinds of edible xanthones, B16F10 cells were treated with α-, β- and γ-mangostin at various concentrations followed by culture for 24 hours. Then, based on MTT β-(4,5-dimethylthiazol-2-yl)-2,5-diphenyltetrazolium bromide) analysis, cell viability was determined. As a result, it was found as shown in FIG. 2 that, in case of a treatment with α- and γ-mangostin, potent cytotoxicity is exhibited at 20 μM and 40 μM while no cytotoxicity is exhibited even at 40 μM in case of a treatment with β-mangostin.

Figure 3:
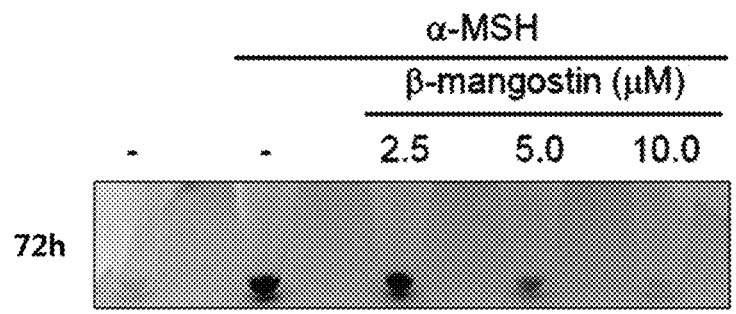
FIG. 3 shows the pellet color change of B16F10 mouse melanoma cells after a treatment with the indicated concentrations of α-MSH and β-mangostin according to one embodiment of the present invention.
Figure 4A:
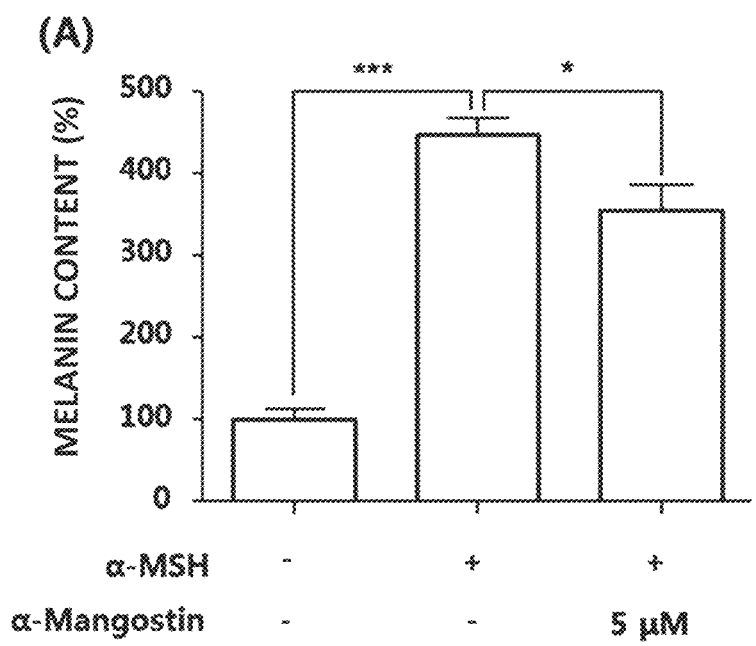
FIG. 4A shows a change in melanin content in B16F10 mouse melanoma cells after a treatment with α-MSH and α-mangostin (A) and γ-mangostin (B) according to one embodiment of the present invention.
Figure 4A:
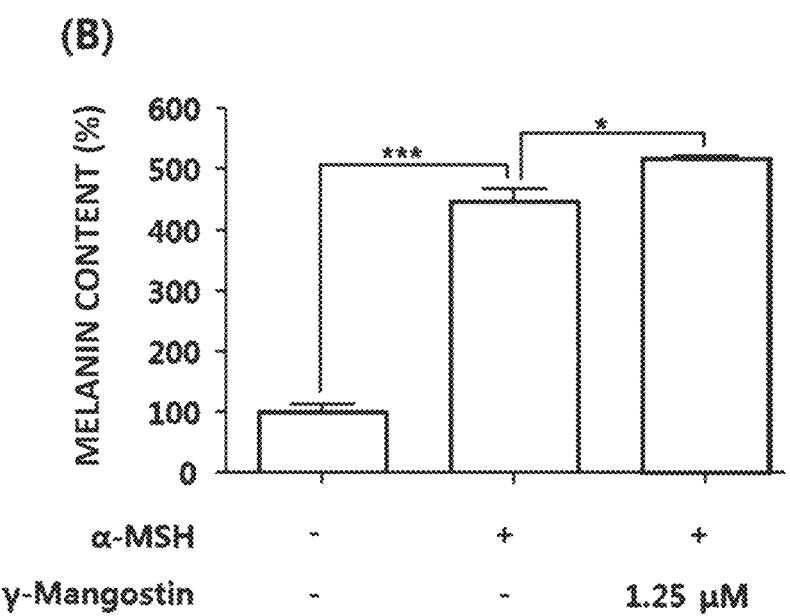
Figure 4B:
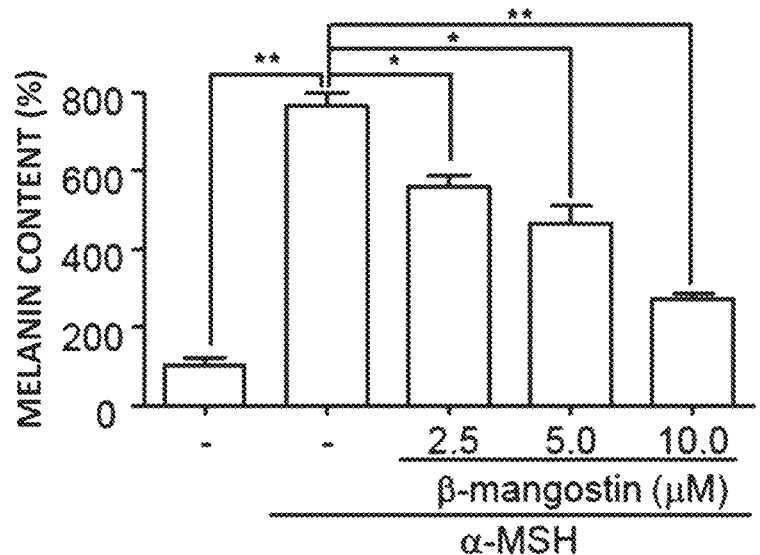
FIG. 4B shows the effect of lowering (A) melanin content and (B) L-DOPA oxidation in B16F10 mouse melanoma cells after a treatment with the indicated concentrations of α-MSH and β-mangostin according to one embodiment of the present invention.
Figure 4B:
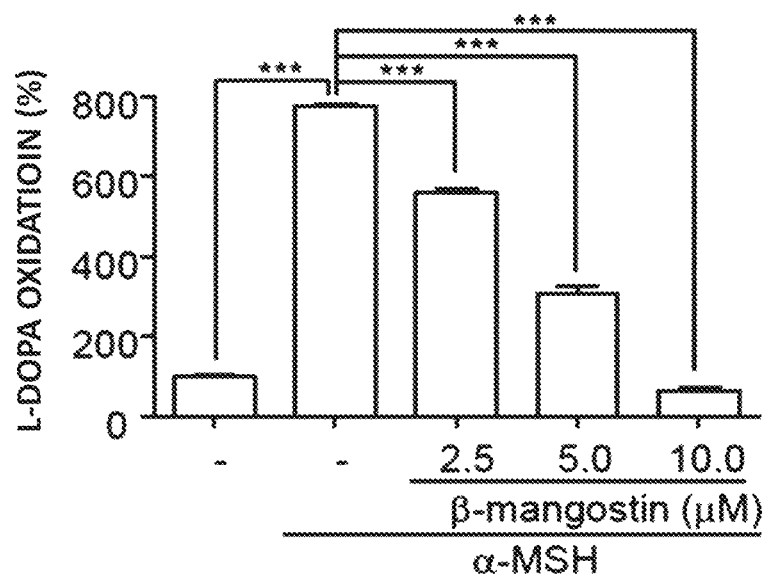

Example 2. Melanin Content Analysis According to Treatment with β-Mangostin of the Present Invention In order to see whether or not β-mangostin can suppress the pigmentation induced by α-MSH (melanocyte-stimulating hormone), B16F10 cells were treated with α-MSH and β-mangostin followed by incubation for 72 hours. As a result, as it is shown in FIG. 3, cell pellets were turned into black color when the treatment is carried out with α-MSH only. However, in case of the treatment together with β-mangostin, pellet color was changed from black color to white color. Namely, it was shown that β-mangostin suppresses the pigmentation induced by α-MSH. Furthermore, as a result of comparing the melanin content lowering effect of α-, β- and γ-mangostin, which are 3 kinds of edible xanthones, it was found that the co-treatment of α-mangostin and α-MSH yields about 20% higher melanin content reduction compared to the treatment with α-MSH only, while γ-mangostin further increased the melanin content (FIG. 4A). On the other hand, β-mangostin of the present invention effectively reduced the melanin content and oxidation level of L-DOPA in concentration dependent manner (FIG. 4B). In particular, when the treatment is carried out with β-mangostin at 5 μM, which is the same concentration as α-mangostin, melanin content was reduced by 40% or so. Thus, it was found that β-mangostin has a more significant whitening activity than α-mangostin. Furthermore, as it has been discussed in Example 1 above, because α-mangostin has a potent cytotoxicity, it is recognized that β-mangostin is more useful than α-mangostin as an industrially useful whitening active component.

Figure 5:
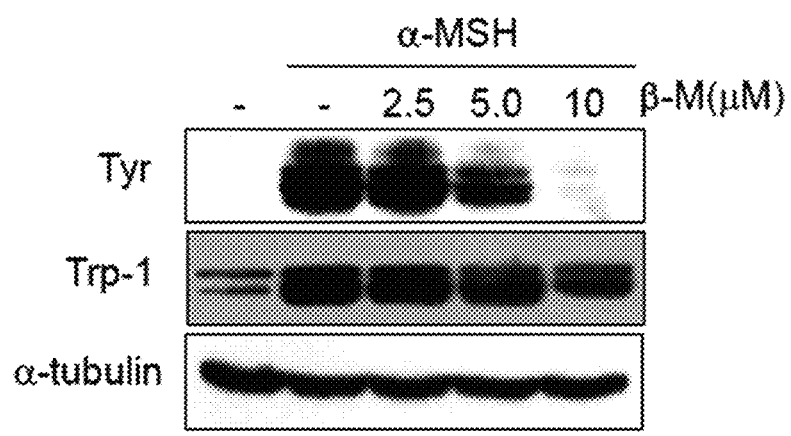
FIG. 5 shows a change in the expression amount of the protein, i.e., tyrosinase (Tyr) and TRP-1 (Trp-1, tyrosinase-related protein-1), in B16F10 mouse melanoma cells after a treatment with different concentrations of α-MSH and β-mangostin according to one embodiment of the present invention. In the figure, α-tubulin indicates a loading control; and β-M indicates beta-mangostin.
Figure 6A:
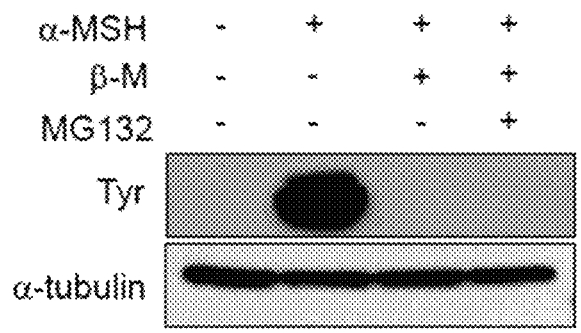
FIGS. 6A to 6C show (A) expression of tyrosinase within B16F10 mouse melanoma cells, (B) melanin content, and (C) oxidation level of L-DOPA after a treatment with α-MSH, β-mangostin and MG132 according to one embodiment of the present invention, wherein the test is carried out to confirm whether or not the decrease in tyrosinase in B16F10 cells is mediated by proteasome. In the figure, α-tubulin indicates a loading control; MG132 indicates a proteasome inhibitor; and β-M indicates beta-mangostin.
Figure 6B:
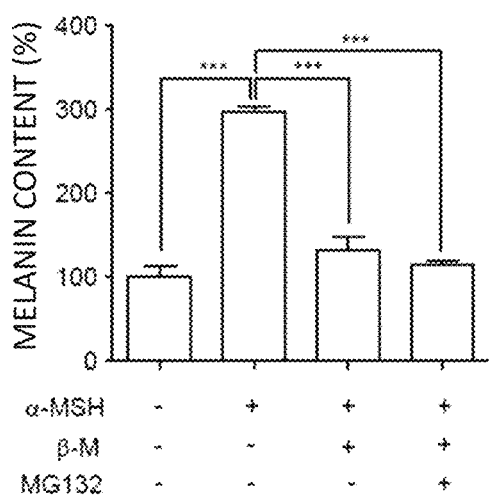
Figure 6C:
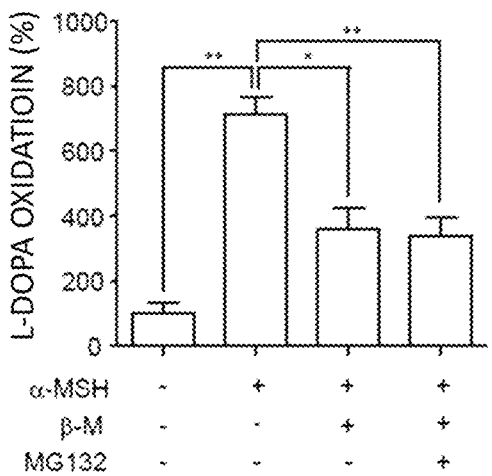

Example 3. Determination of Proteasome-Nondependent Melanosome Removing Effect According to Treatment with β-Mangostin of the Present Invention In order to confirm the whitening effect of β-mangostin, RT-PCR and Western blotting analysis were carried out for tyrosinase and TRP-1. As a result, as it is shown in FIG. 5, the expression amount of tyrosinase and TRP-1, which are induced by α-MSH, was effectively lowered by β-mangostin In order to determine whether or not the aforementioned reduction of tyrosinase is proteasome-mediated or not, a co-treatment of MG132 as a proteasome inhibitor and β-mangostin of the present invention was carried out. As a result, as it is shown in FIG. 6(A), the tyrosinase expression amount did not increase in the cells which have been treated with MG132. As a result of the analysis by measuring the melanin content and L-DOPA oxidation, there was also no influence on the melanin content and L-DOPA oxidation as it is shown in FIGS. 6B and 6C. Based on those results, it was believed that the depigmentation effect of β-mangostin is not mediated by a proteasome, but occurs through other different mechanism.

Figure 7:
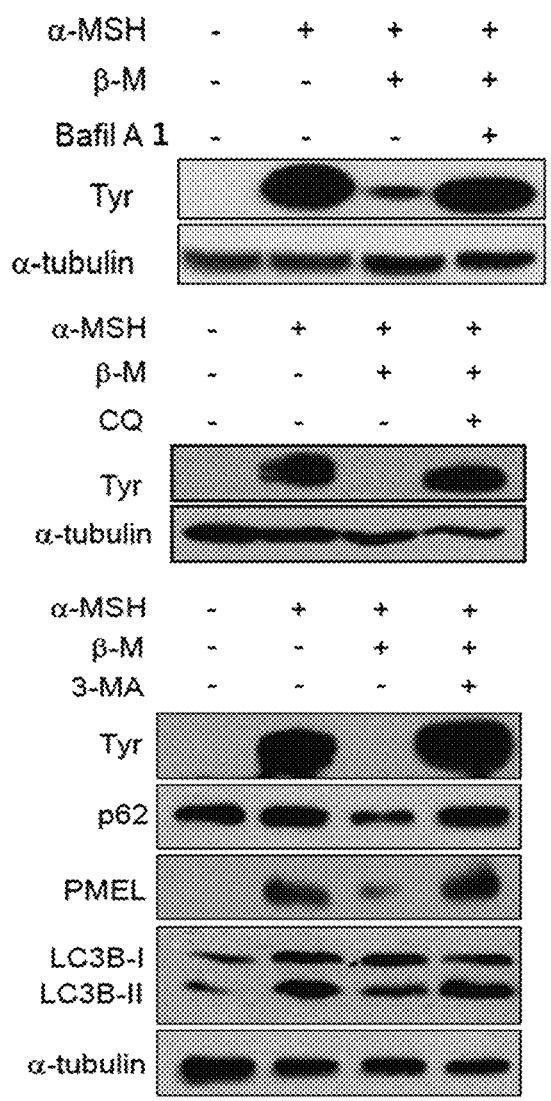
FIG. 7 shows the expression level of tyrosinase, p62, PMEL, LC3B-I and LC3B-II in B16F10 mouse melanoma cells after a treatment with α-MSH, β-mangostin, bafilomycin A1, chloroquine (CQ) and 3-MA β-methyladenine) according to one embodiment of the present invention, wherein the test is carried out to confirm whether or not the depigmentation effect induced by β-mangostin in B16F10 cells is caused by lysosome-dependent proteolysis. In the figure, α-tubulin indicates a loading control; bafilomycin A1, chloroquine, and 3-MA indicate an autophagic activity inhibitor; and β-M indicates beta-mangostin.
Figure 8:
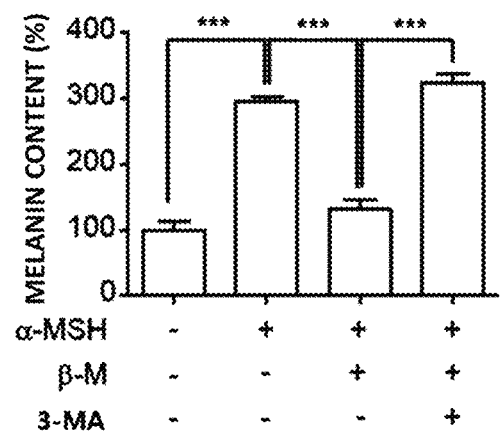
FIG. 8 shows a change in content of melanin in B16F10 mouse melanoma cells after a treatment with α-MSH, β-mangostin and 3-MA β-methyladenine) according to one embodiment of the present invention. In the figure, 3-MA indicates an autophagic activity inhibitor; and β-M indicates beta-mangostin.

Example 4. Determination of Autophagy-Dependent Melanosome Removing Effect According to Treatment with β-Mangostin of the Present Invention Autophagy occurs through a fusion process between an autophagosome and a lysosome. In order to confirm whether or not the depigmentation effect induced by β-mangostin occurs through lysosome-dependent protein degradation during the autophagy process, B16F10 cells were treated with bafilomycin A1 (liquid vacuole type, $H^+$-ATPase inhibitor) which inhibits β-mangostin, α-MSH, and lysosome activity. As a result, as it is shown in FIG. 7, bafilomycin A1 inhibits, at the aforementioned conditions, the suppressed tyrosinase expression that has been induced by β-mangostin. Namely, bafilomycin A1 was found to suppress the fusion between an autophagosomes and a lysosome. Furthermore, chloroquine (CQ) and 3-methyladenine (3-MA), which are other autophagy inhibitors, also inhibited the suppressed expression of tyrosinase which has been induced by β-mangostin, and it was confirmed that they can inhibit the suppressed expression of p62 and PMEL (premelanosome protein) as an autophagy inhibitor marker. It was also found that the melanin content which has been reduced by β-mangostin starts to increase again in the group treated with 3-MA (FIG. 8).

Figure 9:
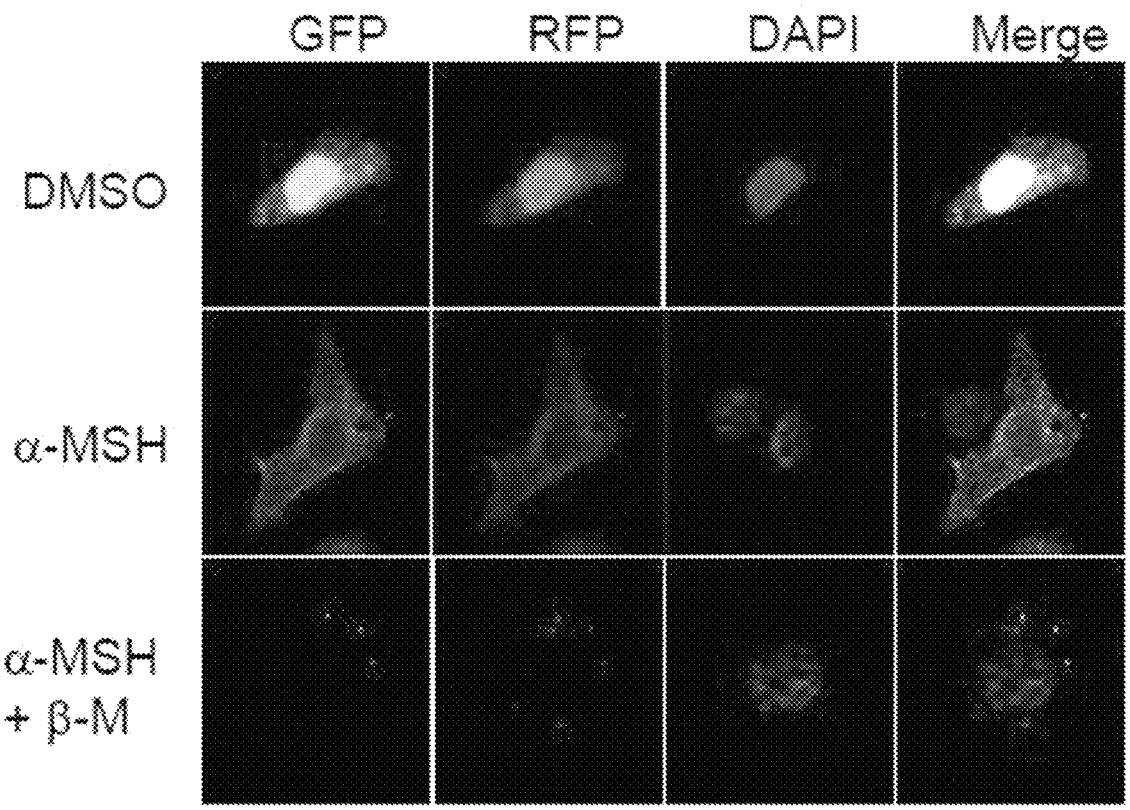
FIG. 9 shows the decomposition of a melasosome caused by self-digestion in a construct expressing mRFP-EGFP-LC3B after a treatment with α-MSH and 3-mangostin according to one embodiment of the present invention.

In order to confirm whether or not β-mangostin can induce the autophagy of a melanosome, B16F10 cells were infected with a construct expressing mRFP-EGFP-LC3B, and then treated with β-mangostin and α-MSH. As a result, as it is shown in FIG. 9, the group treated only with α-MSH showed increased number of yellow spots (melanosome) as LC3BII is related with the formation of melanosome membrane. On the other hand, the number of red spots increased in the group treated with both α-MSH and β-mangostin while total number of spots has decreased. If an autophagosome fuses with a lysosome only after wrapping the melanosome, the intra-autophagosomal pH should decrease, and EGFP should be abolished under acidic pH conditions. Accordingly, it was found from the above results that, due to the autophagy enhanced by β-mangostin, degradation of a melanosome has occurred.

Figure 10A:
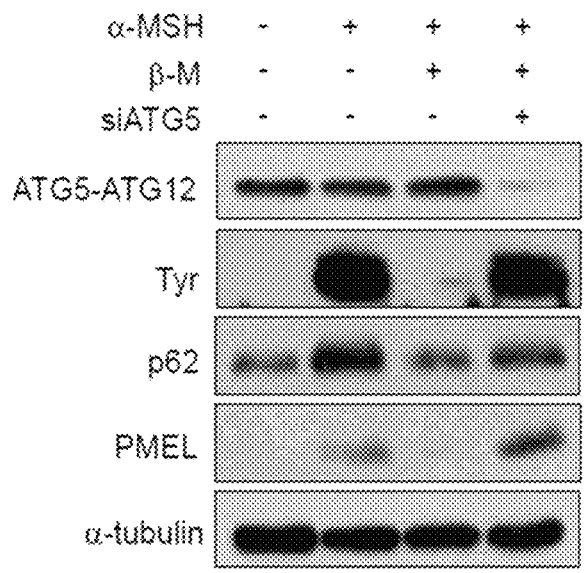
FIGS. 10A and 10B show changes in the level of (A) expression of tyrosinase, p62 and PMEL and (B) melanin content in B16F10 mouse melanoma cells after a treatment with α-MSH and β-mangostin following knockdown of ATG5 (autophagy-related gene 5) that is related to autophagosome elongation according to one embodiment of the present invention, in which the test is carried out to confirm the depigmentation effect caused by an autophagic activity in B16F10 cells as induced by β-mangostin. In the figure, α-tubulin indicates a loading control; and β-M indicates beta-mangostin.
Figure 10B:
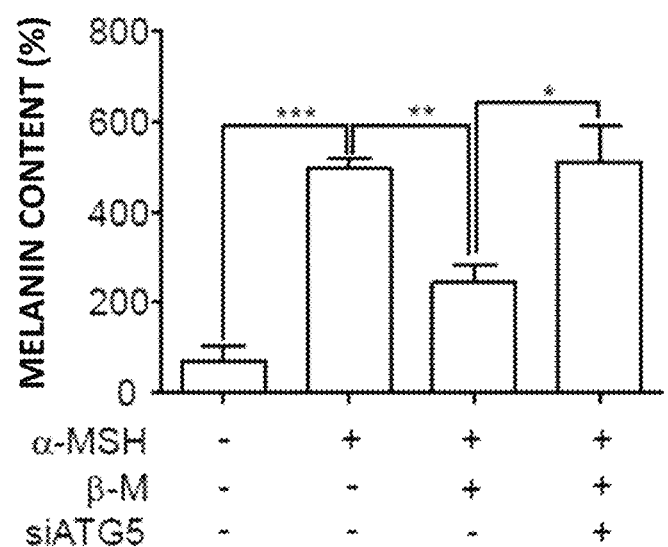

Determination was also made to see whether or not the inhibition on ATG5 (autophagy-related gene 5), which is related with autophagosome elongation playing an important role in autophagy, has any influence on the β-mangostin mediated depigmentation effect. As a result, as it is shown in FIGS. 10A and 10B, knockdown of ATG5 increased again the expression of tyrosinase, p62, and PMEL and melanin content level which have been reduced by the presence of β-mangostin, and the expression amount of ATG5-ATG12, which binds during the process of forming an autophagosome, was lowered. Namely, it was possible to confirm that β-mangostin removes melanin by inducing autophagy in melano cells.

Figure 11A:
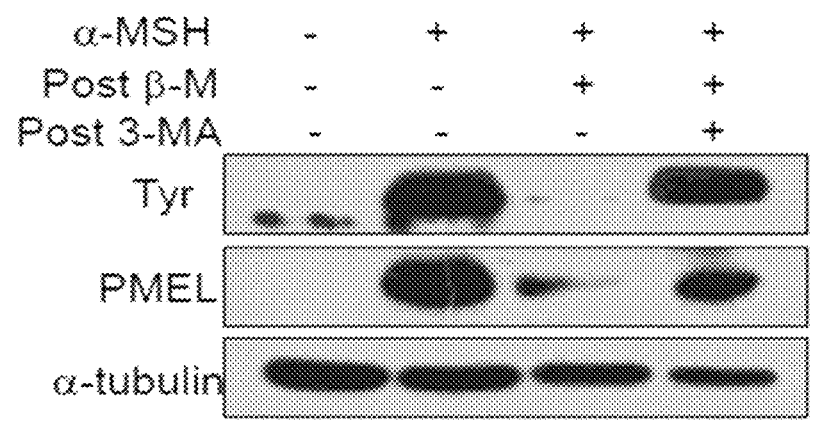
FIGS. 11A and 11B show changes in the level of (A) expression of tyrosinase and PMEL and (B) previously formed melanin content in B16F10 mouse melanoma cells after a treatment with β-mangostin and 3-MA β-methyladenine) following the synthesis of melanin by a treatment with α-MSH according to one embodiment of the present invention. In the figure, α-tubulin indicates a loading control; and β-M indicates beta-mangostin.
Figure 11B:
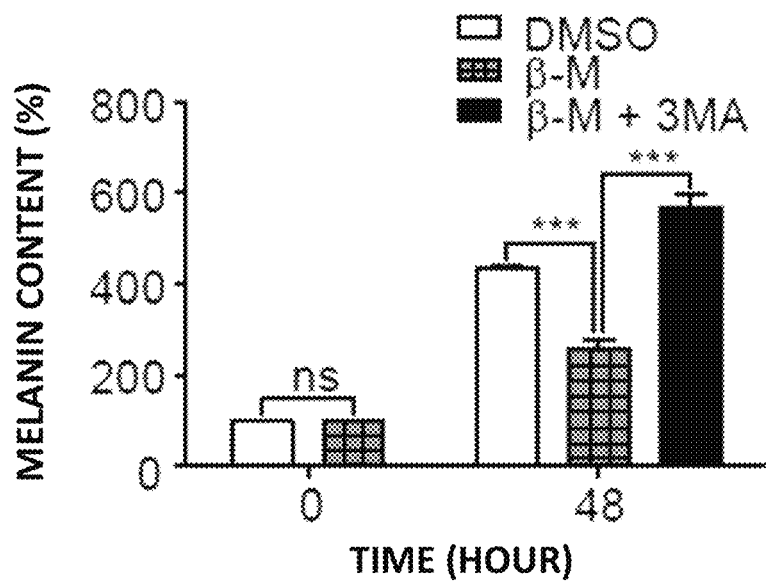

Example 5. Determination of Effect of Removing Previously Produced Melanosome According to Treatment with β-Mangostin of the Present Invention In order to determine the activity of β-mangostin for removing melanin which has been previously produced by α-MSH as a melanin cell stimulating hormone, B16F10 cells were treated for 2 days with α-MSH to have synthesis of melanin. Thereafter, the cells were treated with β-mangostin of the present invention and 3-MA, which is an autophagy inhibitor. As a result, as it is shown in FIGS. 11A and 11B, β-mangostin of the present invention not only can lower a significant expression amount of tyrosinase and PMEL but also can lower effectively the content of previously formed melanin.

It is believed that the autophagy induced by β-mangostin of the present invention can regulate the depigmentation in melanocyte, and the melanosome autophagy-specific inducing agent like β-mangostin can be utilized as a very useful material for developing a skin whitening preparation and a skin lightening preparation.

The invention claimed is:

1. A method of whitening a skin, comprising:
   isolating β-mangostin by extracting seedcases of a mangosteen with chloroform, the β-mangostin represented by the following chemical formula 1;

[Chemical formula 1]

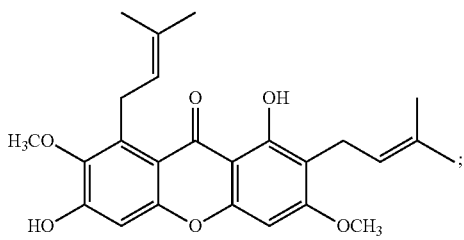

preparing a cosmetic composition comprising:
      the β-mangostin or a cosmetically acceptable salt thereof as an effective ingredient;
      less than 20 μM of α-mangostin; and
      less than 40 μM of γ-mangostin; and
   applying the cosmetic composition to the skin.

2. The method of claim 1, wherein the composition is a formulation selected from the group consisting of a solution, a suspension, an emulsion, a paste, a gel, a crème, a lotion, a powder, a soap, a surfactant-containing cleanser, an oil, a powder foundation, a foundation, a wax foundation, and a spray.

3. A method of whitening a skin, comprising:
   preparing a cosmetic composition comprising xanthone, wherein the xanthone consists of β-mangostin or a cosmetically acceptable salt thereof; and
   applying the cosmetic composition to the skin.

* * * * *